United States Patent [19]

Hiuke

[11] Patent Number: 5,021,051
[45] Date of Patent: Jun. 4, 1991

[54] DISPOSABLE ABSORBENT ARTICLE HAVING IMPROVED BARRIER LEG CUFFS

[75] Inventor: Takashi Hiuke, Osaka, Japan

[73] Assignee: The Procter & Gamble Company, Cincinnati, Ohio

[21] Appl. No.: 334,641

[22] Filed: Apr. 6, 1989

[51] Int. Cl.⁵ .......................................... A61F 13/00
[52] U.S. Cl. .................... 604/385.2; 604/385.1;385.2
[58] Field of Search ............ 604/385 A, 385 R, 385.1, 604/385.2

[56] References Cited

U.S. PATENT DOCUMENTS

| | | |
|---|---|---|
| 2,545,674 | 3/1951 | Ralph . |
| 2,575,164 | 11/1951 | Donovan . |
| 2,916,037 | 12/1959 | Hansen . |
| 3,386,442 | 6/1968 | Sabee . |
| 3,452,753 | 7/1969 | Sanford . |
| 3,530,859 | 9/1970 | Helmowitz .................. 128/284 |
| 3,572,342 | 3/1971 | Lindquist et al. .................. 128/287 |
| 3,593,716 | 7/1971 | Vogt .................. 128/287 |
| 3,658,064 | 4/1972 | Pociluyko .................. 128/287 |
| 3,665,920 | 9/1972 | Davis .................. 128/287 |
| 3,667,466 | 6/1972 | Ralph .................. 128/287 |
| 3,744,494 | 7/1973 | Marsan .................. 128/287 |
| 3,771,524 | 11/1973 | Ralph .................. 128/287 |
| 3,807,402 | 4/1974 | Miller et al. .................. 128/287 |
| 3,825,006 | 7/1974 | Ralph .................. 128/287 |
| 3,828,784 | 8/1974 | Zoephel .................. 128/287 |
| 3,860,003 | 1/1975 | Buell .................. 128/287 |
| 3,920,017 | 11/1975 | Karami .................. 128/287 |
| 3,929,134 | 12/1975 | Karami .................. 128/287 |
| 3,930,501 | 1/1976 | Schaar .................. 128/287 |
| 3,978,861 | 9/1976 | Schaar .................. 128/287 |
| 3,995,640 | 12/1976 | Schaar .................. 128/287 |
| 3,999,547 | 12/1976 | Hernandez .................. 128/284 |
| 4,040,423 | 8/1977 | Jones, Sr. .................. 128/287 |
| 4,041,950 | 8/1977 | Jones, Sr. .................. 128/287 |
| 4,090,515 | 5/1978 | Karami .................. 128/284 |
| 4,210,143 | 7/1980 | De Jonckheere .................. 128/287 |
| 4,326,528 | 4/1982 | Ryan et al. .................. 128/287 |
| 4,413,996 | 11/1983 | Taylor .................. 604/382 |
| 4,490,148 | 12/1984 | Beckestrom .................. 604/385 |
| 4,500,316 | 2/1985 | Damico .................. 604/389 |
| 4,589,876 | 5/1986 | Van Tillburg .................. 604/385 |
| 4,636,207 | 1/1987 | Buell .................. 604/370 |
| 4,657,539 | 4/1987 | Hasse .................. 604/385 A |
| 4,662,877 | 5/1987 | Williams .................. 604/385 A |
| 4,681,579 | 7/1987 | Toussant et al. .................. 604/385 R |
| 4,687,478 | 8/1987 | Van Tillburg .................. 604/387 |
| 4,695,278 | 9/1987 | Lawson .................. 604/385.2 |
| 4,704,115 | 11/1987 | Buell .................. 604/385 A |
| 4,704,116 | 11/1987 | Enloe .................. 604/385 |
| 4,738,677 | 4/1988 | Foreman .................. 604/385 R |
| 4,795,454 | 1/1989 | Dragoo .................. 604/385 R |
| 4,808,177 | 2/1989 | Des Marais et al. .................. 604/385.1 |
| 4,808,178 | 2/1989 | Aziz et al. .................. 604/385.2 |
| 4,816,025 | 3/1989 | Foreman .................. 604/385.2 |
| 4,834,740 | 5/1989 | Suzuki et al. .................. 604/385.2 |
| 4,900,317 | 2/1990 | Buell .................. 604/385.2 |
| 4,909,803 | 3/1990 | Aziz et al. .................. 604/385.2 |

FOREIGN PATENT DOCUMENTS

| | | |
|---|---|---|
| 2561078 | 2/1984 | France . |
| 2159693 | 12/1985 | United Kingdom . |
| 2161059 | 1/1986 | United Kingdom . |
| 2193625 | 2/1988 | United Kingdom . |

*Primary Examiner*—David J. Isabella
*Assistant Examiner*—Gary Jackson
*Attorney, Agent, or Firm*—Steven W. Miller; John M. Pollaro; Fredrick H. Braun

[57] ABSTRACT

A disposable absorbent article, such as a disposable diaper, having barrier leg cuffs. The barrier leg cuffs have a distal edge which is spaced from the proximal edge so as to provide a barrier against leakage. The barrier leg cuff has a portion affixed to the diaper so that the spacing between the barrier leg cuffs is increased in selected portions to reduce irritation of the genetalia and to provide a larger area to receive bodily discharges.

23 Claims, 2 Drawing Sheets

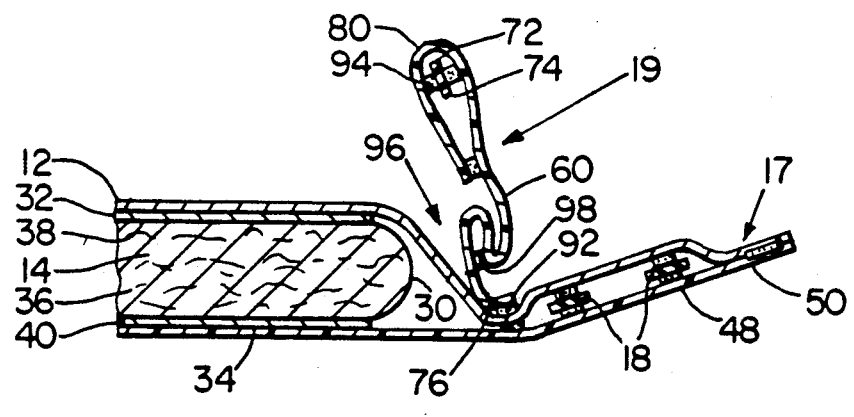

DISPOSABLE ABSORBENT ARTICLE HAVING IMPROVED BARRIER LEG CUFFS

TECHNICAL FIELD

This invention relates to disposable absorbent articles, such as disposable diapers, having barrier leg cuffs and, more particularly, barrier leg cuffs in which a portion of the barrier leg cuff is affixed to the diaper so that the spacing between the barrier leg cuffs is increased in selected portions.

BACKGROUND OF THE INVENTION

Disposable diapers are well known articles of manufacture that are worn by infants and incontinent persons. Disposable diapers are worn about the lower torso and are intended to absorb and contain urine and feces, thereby preventing the urine and feces from soiling, wetting, or otherwise contaminating articles (e.g., clothing, bedding, etc.) that come into contact with the diaper wearer.

In general, disposable diapers all have the same basic structure comprising an absorbent core encased between a liquid permeable, user-contacting topsheet and a liquid impermeable backsheet. The prior art, of course, teaches numerous variations of and elements in addition to the basic topsheet, backsheet, and absorbent core arrangement. For example, an improvement in the performance of disposable diapers has been achieved by the addition of elastic means along portions of the diaper contacting the wearer's thigh, thereby providing elasticized leg openings when the diaper is worn.

When using a disposable diaper having elasticized leg openings, the diaper user fits the diaper on the wearer and fastens it about the wearer's waist thereby effecting a side closure. The elasticized leg openings thereby form gasketing cuffs around the legs of the wearer.

While such diapers are effective in reducing leakage from around the leg opening, a diaper having acceptable containment characteristics may be provided by having a barrier leg cuff instead of, or preferably in addition to, the gasketing cuff. A barrier leg cuff, unlike the aforementioned gasketing cuff, does not form a seal about the wearer's body. Rather, the barrier leg cuff is intended to act as a dam or barrier to the flow of body exudates toward the sides of the diaper. Of course, both concepts may be incorporated into a single diaper having both gasketing cuffs and barrier leg cuffs.

A number of patents have been issued directed to the use of barrier leg cuffs. For example, U.S. Pat. No. 4,704,116 issued to Enloe on Nov. 3, 1987, teaches a diaper having two elasticized portions along each longitudinal portion of the diaper. While it is not clear if the inboard elasticized portion of the aforementioned U.S. Pat. No. 4,704,116 acts as a barrier cuff, it is clear that U.S. Pat. No. 4,695,278 issued to Lawson on Sept. 23, 1987, and U.S. Pat. No. 4,795,454 issued to Dragoo on Jan. 3, 1989, both teach the use of a gasketing cuff and a barrier leg cuff.

The disposable diapers of the prior art, however, lack the aspects of the present invention wherein a portion of the barrier leg cuff is affixed to a portion of the diaper.

It is therefore an object of the present invention to provide a disposable diaper having improved waste containment characteristics.

A further object of the present invention is to provide a disposable diaper having an improved barrier leg cuff.

An additional object of the invention is to provide a disposable diaper in which a portion of the barrier leg cuff is affixed to a portion of the diaper.

These and other objects of the invention will be more readily apparent when considered in connection with the following description and the accompanying drawings.

SUMMARY OF THE INVENTION

According to the present invention, a disposable diaper is manufactured such that an absorbent means is encased between a liquid permeable topsheet and a liquid impermeable backsheet. The diaper is provided with elastic members along its longitudinal sides which form a gasketing cuff around the wearer's legs. In addition, the diaper is provided with a barrier leg cuff. The barrier leg cuff has a proximal edge joined to the diaper between the edge of the absorbent means and the longitudinal sides of the diaper. The distal edge of the barrier leg cuff is spaced from the proximal edge.

The barrier leg cuff has an attachment zone disposed between its proximal and distal edges. The attachment zone is affixed to the diaper at a point between the longitudinal side and the attachment zone. Thus, the spacing between the distal edges of the barrier leg cuffs is increased in selected portions. The portions where the spacing is increased corresponds to that portion of the diaper which will receive the discharge of body exudates and/or the genetalia of the wearer. In addition, since the width (i.e. the distance between the proximal and distal edges) of the barrier leg cuffs is reduced in selected areas to facilitate receiving discharges, a barrier leg cuff having a greater width can be used without increasing the possibility of irritation to the wearer.

BRIEF DESCRIPTION OF THE DRAWINGS

FIG. 4 is a sectional view of an alternative diaper construction corresponding to a section taken along line 3—3 of FIG. 1.

DETAILED DESCRIPTION OF THE INVENTION

Figure 1:
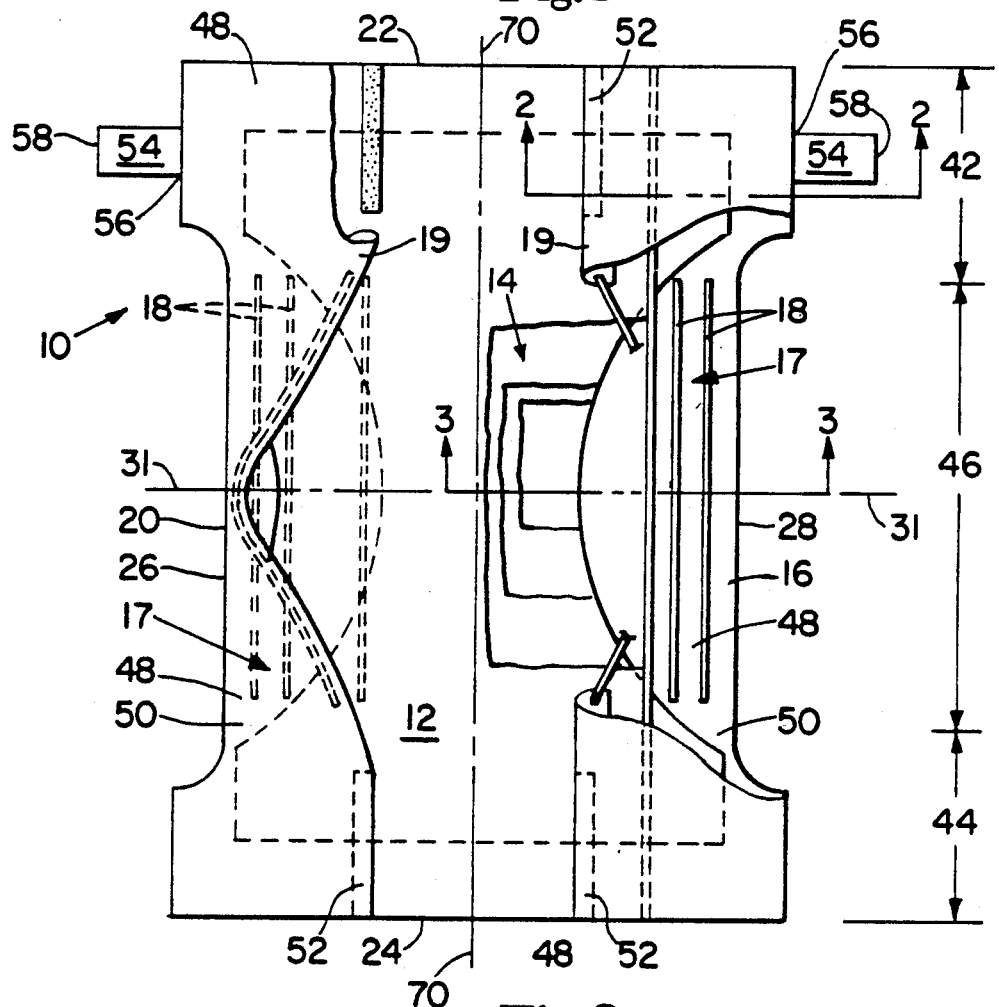
FIG. 1 is a partially cutaway perspective view of an elasticized disposable diaper of the present invention.

Referring now to the drawings, there is shown a preferred embodiment of the present invention as it would be used in a disposable diaper intended to be worn by an infant. As used herein, the term "disposable diaper" refers to a garment generally worn by infants or incontinent persons, which is drawn up between the legs and fastened about the waist of the wearer and further, which is intended to be discarded after a single use (i.e., it is not intended to be laundered or otherwise restored and reused).

FIG. 1 is a partially cut away perspective view of the disposable diaper 10 of the present invention prior to its being folded and placed on the diaper wearer by the diaper user. As can be seen in FIG. 1, a preferred diaper 10 basically comprises a liquid permeable topsheet 12, an absorbent means 14, a liquid impermeable backsheet 16, and a gasketing cuff 17 and a barrier leg cuff 19 corresponding to both the first longitudinal side 26 and the second longitudinal side 28. While the topsheet 12, absorbent means 14, and liquid impermeable backsheet 16 may be assembled in a variety of well known configurations, a preferred disposable diaper configuration is described generally in U.S. Pat. No. 3,860,003 entitled "Contractable Side Portions for Disposable Diaper", issued to K. B. Buell on Jan. 14, 1975, which reference is incorporated herein by reference.

FIG. 1 shows a preferred embodiment of the diaper 10 in which the topsheet 12 and the backsheet 16 are coextensive and have length and width dimensions generally larger than those of the absorbent means 14. The topsheet 12 is superposed on the backsheet 16 thereby forming a periphery 20 of diaper 10. The periphery 20 defines the outer periphery or, in other words, the outer extent of the diaper 10. The periphery 20 comprises first end 22, second end 24, first longitudinal side 26, and second longitudinal side 28. The first end 22 is intended to be positioned at the back of the wearer.

The topsheet 12 may be affixed to the backsheet 16 in any suitable manner as is well known in the diaper manufacturing art. In a preferred embodiment, a multiplicity of longitudinal adhesive bands (not shown) of hot-melt adhesive are applied along the full length of the backsheet 16 generally parallel to the longitudinal centerline 70 of the backsheet 16. The longitudinal adhesive bands serve to affix the topsheet 12 to the backsheet 16 at those points where these three components come together. The extent and location of the points where the topsheet 12, backsheet 16, and longitudinal adhesive bands come together will depend on the spacing between the longitudinal adhesive bands and on the distance the topsheet 12 and the backsheet 16 extend beyond the absorbent means 14. The number of longitudinal adhesive bands and the spacing therebetween should be sufficient to securely bond the topsheet 12 to the backsheet 16 in the area between the periphery 20 and the edge of the absorbent means 14.

A hot-melt adhesive suitable for use as longitudinal adhesive bands is manufactured by Eastman Chemical Products Company, of Kingsport, Tenn. and marketed under the tradename Eastobond A-3. It will be noted that the above described manner of affixing the topsheet 12 to the backsheet 16 causes the topsheet 12 to be affixed to the backsheet 16 intermittently along the first and second ends 22 and 24. The absorbent means 14 is thereby encased between the topsheet 12 and the backsheet 16. Of course, many alternative methods of affixing the topsheet 12 to the backsheet 16 may be used with satisfactory results. For example, the topsheet 12 may be affixed to the backsheet 16 indirectly rather than directly as shown in FIG. 1. Thus, an intermediate member may be used to affix the topsheet 12 to the backsheet 16.

The diaper 10 has first and second waist portions 42 and 44 extending, respectively, from the first end 22 and the second end 24 of the diaper periphery 20 toward the lateral centerline 31 of the diaper 10, a distance from about 1/5 to about ⅓ the length of the diaper. The first and second waist portions 42 and 44 comprise those portions of the diaper 10 which, when worn, encircle the waist of the wearer. The crotch portion 46 is that portion of the diaper 10 between first and second waist portions 42 and 44, and comprises that portion of the diaper 10 which, when worn, is positioned between the legs of the wearer and covers the lower torso of the wearer.

Figure 2:
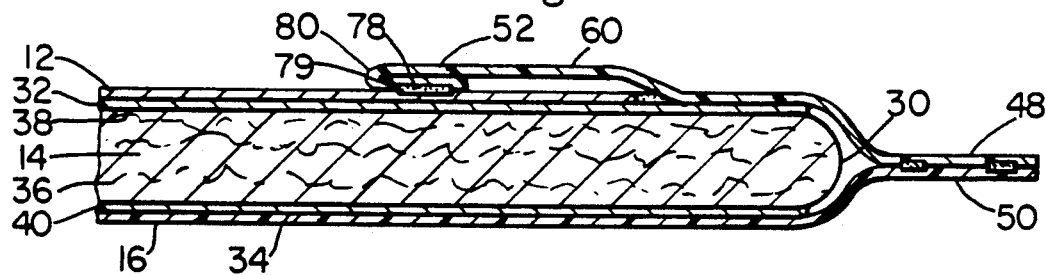
FIG. 2 is a sectional view of the diaper of FIG. 1 taken along line 2—2.
Figure 3:
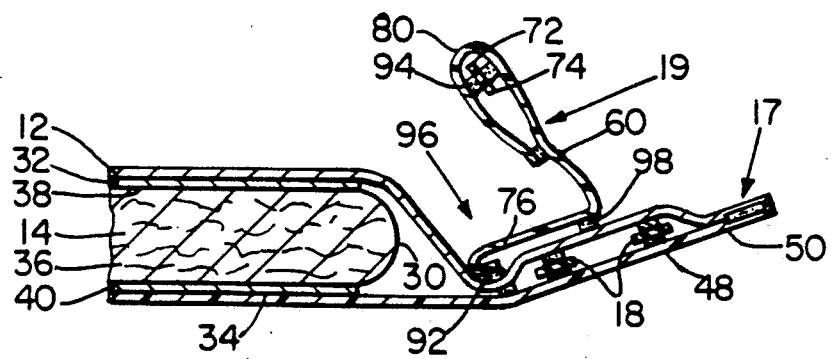
FIG. 3 is a sectional view of the diaper of FIG. 1 taken along line 3—3.

The absorbent means 14 may be any means which is generally compressible, conformable, non-irritating to the wearer's skin, and which is capable of absorbing and retaining liquids. A preferred absorbent means 14, as shown in FIGS. 2, 3, and 4 has first and second opposed faces 32 and 34, respectively, and comprises an absorbent layer 36 and first and second tissue layers 38 and 40, respectively. The first and second tissue layers 38 and 40 overlay the major surfaces of the absorbent layer 36 to o form the first and second opposed faces 32 and 34 of the absorbent means 14. The absorbent means 14 has edges 30 which define the longitudinal periphery of the absorbent means 14.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent layer 36 such as a multiplicity of plies of creped cellulose wadding, polymeric gelling agents, absorbent foams or sponges, or any equivalent material or combination of materials. The total absorbent capacity of the absorbent layer 36 should, however, be compatible with the design liquid loading in the intended use of the disposable diaper 10. Further, the size and absorbent capacity of the absorbent layer 36 may be varied to accommodate wearers ranging from infants through adults.

The preferred embodiment of diaper 10 illustrated in the Figures has an hourglass shaped absorbent layer 36, and is intended to be worn by infants ranging in weight from about 12 to about 26 pounds (about 5 kg to about 12 kg) The absorbent layer 36 is, therefore, a batt of airfelt approximately 16 inches (41 cm) long when measured along the longitudinal centerline 70, approximately 12 inches (32 cm) across the first and second ends 22 and 24, and approximately 4 inches (10 cm) across the narrowest part of the crotch portion 46. The absorptive capacity of the airfelt used for the absorbent layer 36 is sufficient to absorb and retain from about 8 to about 16 grams of water per gram of absorbent material. Accordingly, the airfelt used in the preferred embodiment shown in the Figures weighs from about 30 to about 56 grams and has a generally uniform caliper. It should be understood, however, that the size, shape, configuration, and total absorbent capacity of the absorbent layer 36 may be varied to accommodate wearers ranging from infants through adults. Therefore, the dimensions, shape, and configuration of the absorbent layer 36 may be varied (e.g. the absorbent layer 36 may have a varying caliper, or a hydrophilic gradient, or may contain polymeric gelling agents).

The first and second tissue layers, 38 and 40, are intended to improve the tensile strength of the absorbent means 14 and to reduce the tendency of the absorbent layer 36 to split, lump or ball when wetted. The first and second tissue layers, 38 and 40, also help to improve lateral wicking of liquids, thereby providing a more even distribution of liquid in the absorbent layer 36. While a number of materials and manufacturing techniques may be used to manufacture the first and second tissue layers, 38 and 40, satisfactory results have been obtained with sheets of wet strength tissue paper having a basis weight of approximately 12 pounds per 3000 square feet (16 grams per square meter) and having an air permeability of approximately 100 cubic feet per minute per square foot (30 cubic meters per minute per square meter) over a 0.5 inches (13 mm) water pressure drop. While the first and second tissue layers, 38 and 40, are preferably coterminous with the absorbent layer 36, they may have different dimensions, a different configuration, or they may be omitted entirely.

The absorbent means 14 is superposed on the backsheet 16 and is preferably affixed thereto by any means as is known in the diaper art. For example, the absorbent means 14 can be secured to the backsheet 16 by a uniform continuous layer of adhesive, a patterned layer of adhesive, or an array of lines or spots of adhesive. In the preferred embodiment illustrated in the Figures, the longitudinal adhesive bands used to affix the topsheet 12 to the backsheet 16 may advantageously be used to also affix the absorbent means 14 to the backsheet 16.

The backsheet 16 is impermeable to liquids and prevents liquids absorbed by the absorbent means 14 from wetting the undergarments, clothing, bedding, and other objects which contact the wearer of the disposable diaper 10. Preferably the backsheet 16 is a polyethylene film of from about 0.0005 to about 0.002 inches (about 0.012 to about 0.051 mm) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent means 14 while still preventing liquid from passing through the backsheet 16.

In a preferred embodiment, the backsheet 16 has a modified hourglass shape extending beyond the absorbent layer 36 a minimum distance of at least about 0.5 inches (about 1.3 cm) around the entire diaper periphery 20. The marginal portion 48 is that portion of the diaper 10 between the diaper periphery 20 and the edge of the absorbent layer 36 and comprises longitudinal marginal o portions 50 adjacent first and second longitudinal sides 26 and 28, respectively, in the crotch portion 46.

The topsheet 12 is compliant, soft feeling, and non-irritating to wearer's skin and prevents the wearer of diaper 10 from contacting the absorbent means 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polypropylene), or a combination thereof. Alternatively, the topsheet 12 may be a foam, such as the reticulated foams which are well known in the art or any of the apertured or formed films which are also well known in the art.

A number of manufacturing techniques can be used to manufacture the topsheet 12. For example, the topsheet 12 may be woven, nonwoven, spunbonded, carded, or the like. A preferred topsheet 12 is carded, and thermally bonded by means well known to those skilled in the nonwoven fabrics art. Preferably the topsheet 12 has a weight of from about 18 to about 25 grams per square yard, a minimum dry tensile strength of at least about 400 grams per centimeter in the machine direction and a wet tensile strength of at least about 55 grams per centimeter in the cross machine direction. The diaper 10 is preferably provided with a gasketing cuff 17.

The gasketing cuff 17 is intended to draw the longitudinal marginal portions 50 of the diaper 10 against the wearer's legs to form a seal against leakage. Accordingly, the gasketing cuff 17 is positioned at both the first and second longitudinal sides 26 and 28 of the diaper and comprises the longitudinal marginal portions 50 and elastic members 18. The elastic members 18 are affixed to the longitudinal marginal portions 50 so that they tend to draw and hold the diaper 10 against the legs of the wearer. Thus, when worn, the diaper 10 will have elasticized leg openings which gather the diaper about the wearer's legs thereby forming a gasket to reduce leakage. While this result may be accomplished by any of several means as are well known in the diaper art, a particularly preferred diaper construction incorporating elastic strips is described in detail in the hereinbefore referenced U.S. Pat. No. 3,860,003. In addition, a method and apparatus suitable for manufacturing a disposable diaper having elastic leg bands are described in U.S. Pat. No. 4,081,301 entitled "Method and Apparatus for Continuously Attaching Discrete, Stretched Elastic Strands to Predetermined Isolated Portions of Disposable Absorbent Products", issued to K. B. Buell on Mar. 28, 1978, which patent is incorporated herein by reference.

Relating the teachings of U.S. Pat. No. 3,860,003 to the preferred embodiment shown in the Figures, it can be seen that elastic members 18 are operatively associated with both longitudinal marginal portions 50 in at least the crotch portion 46 in an elastically contractible condition so that in a normally unrestrained configuration the elastic members 18 effectively contract or gather the longitudinal marginal portions 50. (As used herein, the term "operatively associated with" refers to two or more components which act together.)

The elastic members 18 can be operatively associated with the longitudinal marginal portions 50 in an elastically contractible condition in at least two ways. For example, the elastic members 18 can be stretched and while in the stretched condition affixed to the uncontracted and unstretched longitudinal marginal portions 50. Alternatively, the longitudinal marginal portions 50 can be contracted (e.g., by pleating) and then the unstretched elastic members affixed to the contracted longitudinal marginal portions 50.

The elastic members 18 can be affixed to the longitudinal marginal portions 50 in any of several ways which are well known in the art. For example, the elastic members 18 can be ultrasonically bonded or heat sealed into the longitudinal marginal portions 50 using a variety of bonding patterns or the elastic members 18 can simply be glued to the longitudinal marginal portions 50.

In the preferred embodiment illustrated in the Figures, the elastic members 18 are affixed using an adhesive to a portion of the backsheet 16 in the longitudinal marginal portions 50. A suitable adhesive will be flexible and of sufficient adhesiveness to hold the elastic members 18 to the backsheet 16 while the elastic members 18 are stretched. An adhesive which has been used with satisfactory results is manufactured by Findley Adhesives Incorporated of Elm Grove, Wis. and marketed as Findley Adhesives 581-334-01.

Suitable elastic members 18 may be manufactured from a wide variety of elastic materials such as natural rubber, or elastomeric films such as Kraton, ethylene propylene monomer, and polyurethane.

In addition, the elastic members 18 may take a multitude of configurations. For example, the width of the elastic members 18 may be varied from about 0.0015 inches to about 1.0 inches (about 0.038 mm to about 25 mm); the elastic members 18 may comprise a single strip of elastic material or may comprise several parallel or non parallel strips of elastic material; or the elastic members 18 may be rectilinear or curvilinear. One material which has been found to be suitable as an elastic member 18 is an elastic tape having a cross section of 0.007 inches by 0.25 inches (about 0.18 mm by about 6.4 mm) and which is manufactured from natural rubber. Such a product is marketed by Easthampton Rubber Thread Company under the tradename L-1900 rubber compound. The preferred elastic member 18 produces a tensile force of about 100 grams when stretched 100 percent from its relaxed condition.

The diaper 10 is provided with fastening tapes 54 for maintaining the first and second waist portions 42 and 44 in an overlapping configuration when the diaper 10 is worn (See FIG. 1). Thus, the diaper 10 is fitted to the wearer and a side closure formed.

More specifically, the fastening tapes 54 affix the first waist portion 42 to the second waist portion 44 thereby maintaining the first and second waist portions 42 and 44 in an overlapping configuration. Thus, the fastening tapes 54 must be affixed to both the first waist portion 42 and to the second waist portion 44 in a manner and with a strength that is sufficient to resist the forces acting to cause the first and second waist portions 42 and 44 to separate during wearing.

The fastening tapes 54 have a manufacturer's end 56 and a user's end 58. The manufacturer's end 56 is that end of fastening tapes 54 which the manufacturer of the diaper 10 affixes to the diaper 10 while the user's end 58 is that end of fastening tapes 54 which the user affixes to the diaper 10 when fitting it to the wearer. The manufacturer's end 56 can be affixed to the first waist portion 42 by any suitable method known in the art, such as by using ultrasonic bonding, heat sealing, or pressure-sensitive adhesives, which are preferred. After fitting the diaper 10 about the waist of the wearer, the user's end 58 is affixed to the second waist portion 44 thereby causing the diaper 10 to encircle the waist of the wearer and effecting a side closure.

As can be seen in FIG. 3, the diaper 10 is provided with a barrier leg cuff 19 along each of the first and second longitudinal sides 26 and 28 respectively. The barrier leg cuffs 19 provide a barrier to restrain the free flow of body exudates before they reach first and second longitudinal sides 26 and 28 and provide a structure to hold and contain such exudates within the diaper 10. The barrier leg cuffs 19 function differently from the gasketing cuffs 17. The gasketing cuffs 17 will generally remain in the same place as the diaper 10 and form a seal against leakage by drawing the diaper against the wearer's skin. The barrier leg cuffs 19 are intended to be disposed out of the plane of the diaper 10 (i.e. the plane in which body exudates will flow) and thereby provide a barrier or dam against leakage. Thus, liquid such as urine flowing across the topsheet 12 will encounter the barrier leg cuff 19 and be stopped and leakage will not occur unless the urine, for example, can flow over the barrier leg cuff 19.

The higher the dam, the more effective it is. Therefore, the greater the width (i.e. the distance between the proximal and distal edges 76 and 80 respectively) of the barrier leg cuff 19, the more effective the barrier leg cuff 19 will be. There is, however, a negative associated with relatively wide barrier leg cuffs 19 in that they tend to contact and irritate the genetalia of the wearer.

Referring now to FIGS. 3 and 4, each barrier leg cuff 19 is flexible, preferably having a body portion 60, a proximal edge 76, a distal edge 80, and a spacing means 72 such as a spacing elastic member 74. Preferably the spacing means 72 is a spacing elastic member 74 in which case the body portion 60 is contractible. The barrier leg cuffs 19 may be manufactured from a wide variety of materials such as polyethylene, polypropylene, polyester, rayon, nylon, foams, plastic films, formed films, and elastic foams. A number of manufacturing techniques may be used to manufacture the barrier leg cuffs 19. For example, the barrier leg cuffs 19 may be woven, nonwoven, spunbonded, carded or the like. While the barrier leg cuff 19 may be liquid permeable, a particularly preferred barrier leg cuff 19 is a nonwoven polypropylene material containing no finish or surfactant to render it liquid impermeable. A particularly preferred nonwoven polypropylene material is manufactured by Crown Zellerbach Company and marketed under the tradename Celestra.

As shown in FIG. 3, the barrier leg cuff 19 and, more particularly, the proximal edge 76, is positioned on the longitudinal marginal portions 50. The barrier leg cuff 19 may, of course, be positioned between the corresponding first or second longitudinal side 26 or 28 respectively and the longitudinal centerline 70 of the diaper 10 provided, however, that the spacing between the distal edges 80 is sufficiently wide to allow urine and/or feces to be received. In the preferred embodiment illustrated having a gasketing cuff 17, the proximal edge 76 is preferably positioned between the inboardmost edge of the elastic members 18 and the edge of the absorbent layer 36. The term "inboard" is defined as the direction toward the centerline of the diaper 10 that is parallel to the respective edge of the diaper 10.

As used herein, the term "corresponding" is used to refer to elements which are associated with each other. Thus, for example, two barrier leg cuffs 19 are provided in the preferred embodiment -- one barrier leg cuff 19 corresponds to the first longitudinal side 26 and one corresponds to the second longitudinal side 28.

The proximal edge 76 and the distal edge 80 are in spaced relation to each other and define the width of the barrier leg cuff 19. The proximal and distal edges 76 and 80, respectively, may be in a parallel, non parallel, rectilinear or curvilinear relationship. In addition, the barrier leg cuff 19 may have a variety of different cross sectional areas including circular, square, rectangular or any other shape. Preferably, the proximal edge 76 is spaced from the distal edge 80 in a parallel and rectilinear relationship to provide a barrier leg cuff 19 having uniform widths. Each barrier leg cuff 19 preferably has a width of from about 5 mm to about 90 mm, and preferably from about 20 mm to about 60 mm. In general, the width of the barrier leg cuff 19 should be as large as is practical. Larger widths, however, increase the possibility of the discharge of body exudates occurring on the barrier leg cuff 19 rather than on the topsheet 12. In addition, barrier leg cuffs with larger widths are more likely to contact the genitals of the wearer and cause irritation. The disadvantages associated with wide barrier leg cuffs 19 can, however, be reduced and preferably eliminated by the use of attachment zones 98 as hereinafter described.

The preferred embodiment of the diaper 10 shown in FIG. 3 is provided with the barrier leg cuff 19 joined to the topsheet 12. The term "joined" includes any means for affixing the barrier leg cuff 19 to the diaper 10 and includes embodiments wherein the barrier leg cuff 19 is a separate element having the proximal edge 76 directly or indirectly attached to the topsheet 12 (i.e., integral) or embodiments wherein the barrier leg cuff 19 is made from the same element or material as the topsheet 12 so that the proximal edge 76 is a continuous and undivided element of the topsheet 12 (i.e., unitary). The barrier leg cuff 19 may alternatively be Joined to the gasketing cuff 17, the backsheet 16, the absorbent layer 36, or any combination of these or other elements of the diaper 10. In a preferred diaper 10, the barrier leg cuffs 19 are integral with the topsheet 12. The integral barrier leg cuff 19 is preferably formed by a single strip of material which is secured to the topsheet 12 by any suitable means such as adhesive 92, the distal edge 80 being formed by folding an end of the material back upon itself.

The distal edge 80 is preferably disposed inboard of the proximal edge 76 and is more preferably inwardly directed to present a more o effective barrier against the flow of exudates. While the distal edges 80 may alternatively be disposed in other positions in relation to the proximal edges 76, such positions are not preferred.

The distal edge 80 is preferably not secured to any other element in at least the crotch portion 46 of the diaper 10 so that it may be spaced away from the proximal edge 76. The distal edge 80 is preferably spaced away from the proximal edge 76 so that the barrier leg cuff 19 may form a channel 96 to enhance the containment of the article. As used herein, "spaced" includes an embodiment wherein the distal edges 80 may assume one or more positions relative to the proximal edge 76 including at some times assuming a position adjacent the proximal edge 76 provided that the distal edge 80 is not in the general plane of the diaper 10 while the proximal edge 76 is in the general plane of the diaper 10. The distance between the distal edge 80 to the proximal edge 76 is measured along a line drawn from the distal edge 80 to the closest part of the proximal edge 76 when the distal edge 80 is positioned so a$ to be spaced away from the proximal edge 76 as far as possible (i.e., in the elastically contracted position). Preferably, the distal edge 80 is spaced away from the proximal edge 76 by a height of at least about 2 mm, and more preferably of from about 5 mm to about 50 mm. The channel 96 forms a barrier to the flow of exudates as they bend to move or float across the topsheet 12. Thus the channel 96 holds and contains exudates until the diaper 10 can be removed.

The barrier leg cuff 19 may additionally be provided with absorbent material secured to or within the barrier leg cuff 19. The absorbent material absorbs and contains exudates which contact the barrier leg cuff 19. The absorbent material may be any material which is capable of absorbing and retaining liquid and may have any size, shape, configuration or absorbent capacity. The absorbent material may be positioned along the inboard surface of the barrier leg cuff 19 or within the barrier leg cuff 19. Preferably, the absorbent material is a layer of airfelt secured within the tunnel formed by the integral barrier leg cuff 19 and secured along the entire length and width of the inboard surface of the barrier leg cuff 19.

In addition, the barrier leg cuff 19 may be rendered liquid impermeable so as to prevent the strikethrough of body exudates. A liquid impermeable barrier leg cuff 19 retards the movement of liquid through the barrier leg cuff 19, thereby making it more leakage resistant. The barrier leg cuff 19 may be rendered liquid impermeable in any manner well known in the art such as selectively treating the barrier leg cuff 19 with a material which will render it liquid impermeable, treating the barrier leg cuff 19 to remove surfactants or other treatments which render the barrier leg cuff 19 liquid permeable, or by securing a separate liquid impermeable material to the barrier leg cuff 19.

The spacing means 72 for spacing the distal edge 80 away from the proximal edge 76 is any member which gathers, contracts, stiffens, shortens or otherwise acts on the barrier leg cuff 19 so as to cause a channel 96 to be formed along the barrier leg cuff 19.

As shown in the Figures, the spacing means 72 preferably comprises the spacing elastic member 74 secured adjacent the distal edge 80 inside of the barrier leg cuff 19. The spacing elastic member 74 is preferably secured to the barrier leg cuff 19 in an elastically contractible condition so that in a normally unrestrained configuration, the spacing elastic member 74 effectively contracts or gathers the barrier leg cuff 19. The spacing elastic member 74 can be secured to the barrier leg cuff 19 in an elastically contractible condition in at least two ways as is discussed in the above referenced U.S. Pat. No. 3,860,003 issued to K. B. Buell. In addition, the length of the spacing elastic member 74 in general is dictated by the diaper design. In the embodiment illustrated in the Figures, the spacing elastic member 74 extends essentially the entire length of the barrier leg cuff 19 in the crotch portion 46, although other lengths may be used.

As shown in FIGS. 3 and 4, the spacing elastic member 74 is associated with the barrier leg cuff 19 by securing it within the barrier leg cuff 19 with elastic attachment means 94. While the spacing elastic members 74 may be secured to the barrier leg cuff 19 adjacent only the ends of the elastic spacing member 74, it is preferable to secure the entire length of the spacing elastic member 74 to the barrier leg cuff 19. The elastic attachment means 94 herein are preferably glue beads made of hot melt adhesive such as marketed by Findley Adhesives Incorporated, Elmgrove, Wis., as Findley Adhesives 581. A more detailed description of the manner in which the spacing elastic members 74 may be positioned and secured to the barrier leg cuff 19 can be found in U.S. Pat. No. 4,081,301 issued to Buell on Mar. 28, 1978, and in U.S. Pat. No. 4,253,461 issued to Strickland et al. on Mar. 3, 1981, both of which patents are incorporated herein by reference. It should also be noted that one or more spacing elastic members 74 can be used to elasticize each barrier leg cuff 19.

Spacing elastic members 74 which have been found suitable are elastic strands having a cross section of 0.18 mm by 1.5 mm and made from natural rubber as available from Easthampton Rubber Company of Stewart, Va., under the tradename L-1900 Rubber Compound. Other suitable spacing elastic members 74 can be made from natural rubber, such as elastic tape sold under the tradename Fulflex 9211 by Fulflex Company of Scotland, N.C. The spacing elastic members 74 may also comprise any heat shrinkable elastic material as is well known in the art. Other suitable elastic materials may comprise a wide variety of materials as are well known in the art include Lycra elastomeric films, polyurethane films, elastomeric foams and formed elastic scrim.

In addition, the spacing elastic members 74 may take a multitude of configurations. For example, the width of the spacing elastic members 74 may be varied; the spacing elastic members 74 may comprise a single strand or several parallel or non-parallel strands of elastic material; or the spacing elastic members 74 may be rectilinear or curvilinear. Still further, the spacing elastic members 74 may be affixed to the barrier leg cuff 19 in any of several ways which are well known in the art. For example, the spacing elastic members 74 may be ultrasonically bonded or heat sealed into the barrier leg cuff 19 using a variety of bonding patterns, or the spacing elastic members 74 may simply be glued to the barrier leg cuffs 19.

The spacing means 72 for spacing the distal edge 80 away from the proximal edge 76 may alternatively comprise several other elements. For example, the barrier leg cuff 19 may have a stiffening element disposed in or on each barrier leg cuff 19. The stiffening element must be sufficiently stiff so that the distal edge 80 is spaced away from the proximal edge 76. Suitable materials for the stiffening element include foams, nonwoven fabrics, batting, polyethylene film, formed films, spray glues, foamed elastomerics, polyester, polyurethane, or a high loft material as is manufactured by Carolina Formed Fabrics.

The spacing means 72 may also comprise means for shortening the length of the distal edge 80 in comparison to the length of the first and second longitudinal sides 26 and 28 of the diaper 10. The distal edge 80 can be shortened by making a fold or pleat in the distal edge 80. This fold or pleat is secured by any of the holding means well known to those of ordinary skill in the art, such as adhesives or heat sealing. Alternatively, a section may be cut out of the distal edge 80 and the distal edges 80 brought together to form a butt or lap joint. The distal edge 80 may also be shortened by attaching a length of the distal edge 80 to the topsheet 12 at a position different from where the distal edge 80 would lie when the diaper 10 is in a flattened out condition. Other shortening techniques as are known in the art may also be used.

Each barrier leg cuff 19 has an attachment zone 98. The attachment zone 98 is positioned between the distal edge 80 and the proximal edge 76 of the barrier leg cuff 19. While the dimensions and shape of the attachment zone 98 are not critical, it has been found that a generally rectangular shape having dimensions of 30 mm by 1 mm is suitable. It should, of course, be understood that other shapes and dimensions may be equally suitable. While the position of the attachment zone 98 along the length of the barrier leg cuff 19 may be varied, it has been found that for diapers 10 intended to be worn by boys, the center of the attachment zone 98 should preferably be from about 250 mm to about 380 mm from the first end 22. For diapers 10 intended to be worn by girls, the attachment zone 98 should preferably be from about 150 mm to about 300 mm from the first end 22. For diapers 10 intended to be worn by both boys and girls, the attachment zone 98 should preferably be from about 150 mm to about 380 mm and most preferably from about 200 mm to about 340 mm from the first end 22.

The attachment zone 98 is bonded to the diaper 10 in an area between the attachment zone 98 and the first longitudinal side 26 or second longitudinal side 28 whichever corresponds to the attachment zone 98 under consideration. As can be seen in FIG. 3, a preferred embodiment results when the attachment zone 98 is affixed to the diaper 10 in an area between the proximal edge 76 and the corresponding first or second longitudinal side 26 or 28 respectively. FIG. 4 shows an alternatively preferred embodiment in which the attachment zone 98 is affixed to the diaper in an area between the attachment zone 98 and the proximal edge 76.

The attachment zone 98 is preferably coated with an adhesive which is suitable for bonding the barrier leg cuff 19 to another component of the diaper 10. An adhesive which has been found suitable is marketed by H. B. Fuller Company under the tradename HM-6515. The attachment zone 98 may, of course, be bonded to the diaper 10 in any other suitable fashion such as by ultrasonic bonding techniques.

The object in choosing the location, size, and shape of the attachment zone 98 is to provide a portion of the barrier leg cuff 19 which has an increased spacing between the distal edges 80 of the barrier leg cuffs 19 in that portion of the barrier leg cuff 19 which corresponds to the genital area of the wearer. Such an arrangement provides easier accommodation of the genitals thereby reducing the possibility of irritation. In addition, the possibility of urine discharge on the outer portion of the barrier leg cuff 19 is reduced.

As can be seen in FIGS. 1 and 2, the barrier leg cuff 19 preferably has secured portions 52. Preferably, the secured portions 52 are located in the first waist portion 42 and second waist portion 44. The secured portions 52 are those portions of the body portion 60 which are affixed to the diaper Preferably, the secured portions 52 are affixed to the topsheet 12 by adhesive means 78 and are intended to maintain the barrier leg cuff 19 in a configuration where the distal edge 80 is inboard of the proximal edge 76. Accordingly, the body portion 60 is adhered to the diaper 10 such that it is directed inboard from the first and second longitudinal sides 26 and 28 respectively.

The adhesive means 78 provide a more comfortable fit for the wearer and reduce the possibility of inversion of the distal edges 80 of the barrier leg cuffs 19 during application and use. Inversion is generally defined as the inboard disposed distal edge 80 turning outwardly when the diaper 10 is applied to the wearer. In a preferred embodiment as shown in the Figures, such adhesive means 78 are disposed in the first waist portion 42 and the second waist portion 44 of the diaper 10. The remaining portions of the barrier leg cuff 19 are not secured so that the distal edges 80 are left free. In a preferred embodiment, the secured portions 52 extend through the entire first waist portion 42, but through only a portion of the second waist portion 44. This construction is preferred so as to create a channel 96 around the buttocks of the wearer to especially prevent leakage of loose fecal material.

The adhesive means 78 are preferably glue beads 79 consisting of hot melt adhesives such as those marketed by Findley Adhesives Incorporated, Elmgrove, Wis., as Findley Adhesives 581. Other means of securing the distal edge 80 to the diaper 10 may also be used.

The diaper 10 is applied to a wearer by positioning the first waist portion 42 under the wearer's back, and drawing the remainder of the diaper 10 between the wearer's legs so that the second waist portion 44 is positioned across the front of the person. The ends of the fastening tapes 54 are then secured preferably to outwardly facing areas of the diaper 10. In this manner, the barrier leg cuffs 19 should be disposed in the crotch portion 46 of the wearer and should provide the dispositions and functions described hereinbefore. Once applied, the distal edges 80 of the barrier leg cuffs 19 extend through the groin areas and diverge upwardly along both of the buttocks of the wearer. Neither of the barrier leg cuffs 19 encircle the thighs of the wearer. However, the gasketing cuffs 17 will encircle the thighs and create a gasketing action against the thighs. The ends of the barrier leg cuff 19 are secured to the topsheet 12 to obviate the inversion of the barrier leg cuffs 19 or comfort for the wearer during application and use and for ease of application.

The gasketing cuffs 17 ride down on the legs and encircle the thighs of the wearer. The barrier leg cuffs 19 ride up on the legs and run through the crotch portion 46 and diverge upwardly over both the buttocks of the wearer. The barrier leg cuffs 19 do not encircle the thighs of the wearer. The distal edges 80 are spaced away from the flow path of body exudates discharged onto the topsheet 12 and lie against the perineum of the wearer. The barrier leg cuffs 19 are, therefore, pushed snugly against the perineum of the wearer in the crotch portion 46 of the diaper 10. The size of the channel 96 is enhanced by the resiliency of the absorbent layer 36 which tends to push itself away from the perineum. This results in the diaper 10 having channels 96 extending along the crotch portion 46 of the wearer. Therefore, body exudates are restrained from penetrating beyond the barrier leg cuffs 19 because the channels 96 form a barrier to the flow of exudates.

Basically, without intending to limit the present invention, the present invention is a diaper that is especially useful and leakage resistant against loose fecal material, the improved containment characteristics being achieved in the following manner. As loose fecal material is discharged onto the topsheet 12, the material flows or floats on the topsheet 12. (Hereinafter referred to as surface material.) The surface material moves from the point of discharge toward the first and second longitudinal sides 26 and 28. Surface material will contact the barrier leg cuff 19 along the inboard surface. In normal use, gravitational forces will tend to cause the surface material to collect in the channel 96 formed by the standing barrier leg cuff 19; the material being held in the channels 96 until the diaper 10 can be removed. Improved containment is achieved because surface material would have to flow up the channel 96, which direction is substantially directly against the force of gravity when the wearer is in an upright position, in order to penetrate and flow over the distal edges 80 of the barrier leg cuffs 19. However, should such material flow beyond the barrier leg cuffs 19, it is retarded from leaking out of the diaper 10 by the gasketing effect achieved by the gasketing cuffs 17, as they draw and gather the first and second longitudinal sides 26 and 28 about the legs of the wearer, thereby providing a second and independent effective barrier against leakage so as to further prevent the soiling of adjacent garments.

While particular embodiments of the present invention have been illustrated and described, it would be obvious to those skilled in the art that various other changes and modifications can be made without departing from the spirit and scope of the invention.

What is claimed is:

1. A unitary disposable absorbent article comprising:
    a liquid permeable topsheet;
    a liquid impermeable backsheet affixed to said topsheet;
    an absorbent means for absorbing liquids, said absorbent means being encased between said topsheet and said backsheet;
    a first end, a second end opposed to said first end, a first longitudinal side and a second longitudinal side;
    a barrier leg cuff corresponding to each of said first and second longitudinal sides, each said barrier leg cuff having a proximal edge affixed to the absorbent article, a distal edge spaced from said proximal edge, and an attachment zone disposed between said proximal edge and said distal edge, said attachment zone being affixed to the absorbent article in an area between said the portion of said barrier cuffs that is between said attachment zone and said proximal edges and said longitudinal side corresponding to said attachment zone so as to increase the lateral spacing between said distal edges along a portion of the length of the absorbent article; and
    a spacing means operatively associated with each said barrier leg cuff in an elastically contractible condition for spacing said distal edge away from said proximal edge 2. The disposable absorbent article of claim 1 wherein said attachment zone is positioned along the length of said barrier cuff from about 150 mm to about 380 mm from said first end.

3. The disposable absorbent article of claim 2 wherein said attachment zone is positioned along the length of said barrier leg cuff from about 200 mm to about 340 mm from said first end.

4. The disposable absorbent article of claim 2 wherein said attachment zone is positioned along the length of said barrier leg cuff from about 250 mm to about 380 mm from said first end.

5. The disposable absorbent article of claim 2 wherein said attachment zone is positioned along the length of said barrier leg cuff from about 150 mm to about 300 mm from said first end.

6. The disposable absorbent article of claim 1 wherein the width of each said barrier leg cuff is from about 5 mm to about 90 mm.

7. The disposable absorbent article of claim 6 wherein the width of each of said barrier cuffs is from about 20 mm to about 60 mm.

8. The disposable absorbent article of claim 1 wherein said spacing means is a spacing elastic member.

9. The disposable absorbent article of claim 1 wherein said attachment zone is affixed to an area of said barrier leg cuff between said (attachment zone) and said proximal edge.

10. The disposable absorbent article of claim 1 further comprising an elastically contractible gasketing cuff along each of said first and second longitudinal sides, each said elastically contractible gasketing cuff comprising a longitudinal marginal portion and an elastic member operatively associated in an elastically contractible condition with said longitudinal marginal portion.

11. The disposable absorbent article of claim 10 wherein each said elastically contractible gasketing cuff comprises an elastic member operatively associated with a longitudinal marginal portion.

12. The disposable absorbent article of claim 1 wherein said attachment zone is affixed to the absorbent article in an area between said proximal edge and said corresponding longitudinal side.

13. The disposable absorbent article of claim 1 wherein said proximal edge is disposed between said absorbent means and said longitudinal side.

14. The disposable absorbent article of claim 1 wherein said barrier leg cuff is liquid impermeable.

15. The disposable absorbent article of claim 1 wherein said barrier leg cuff is integral with said topsheet.

16. The disposable absorbent article of claim 1 wherein said barrier leg cuff is unitary with said topsheet.

17. A unitary disposable diaper comprising:
a liquid permeable topsheet;
a liquid impermeable backsheet affixed to said topsheet;
an absorbent means for absorbing liquids, said absorbent means being encased between said topsheet and said backsheet;
a first end, a second end opposed to said first end, a first longitudinal side and a second longitudinal side;
a barrier leg cuff corresponding to each of said first and second longitudinal sides, each said barrier leg cuff having a proximal edge affixed to the absorbent article, a distal edge spaced from said proximal edge, and an attachment zone disposed between said proximal edge and said distal edge, said attachment zone being affixed to the diaper in an area between said the portion of said barrier cuffs that is between said attachment zone and said proximal edges and said longitudinal side corresponding to said attachment zone so as to increase the lateral spacing between said distal edges along a portion of the length of the diaper, said attachment zone being positioned along the length of said barrier leg cuff from about 150 mm to about 380 mm from said first end, and the width of each of said barrier leg cuffs being from about 5 mm to about 90 mm; and
a spacing elastic member operatively associated in an elastically contractible condition with each said barrier cuff for spacing said distal edge away from said proximal edge.

18. The disposable diaper of claim 17 additionally comprising an adhesive means for reducing the possibility of inversion of said distal edges of said barrier leg cuffs during application and use, said adhesive means being disposed in both said first end and said second end of the diaper.

19. The disposable diaper of claim 18 wherein said barrier leg cuff is integral with said topsheet.

20. The disposable diaper of claim 19 wherein said attachment zone is affixed to an area of said barrier leg cuff between said attachment zone and said proximal edge.

21. The disposable diaper of claim 19 wherein said attachment zone is affixed to the diaper in an area between said proximal edge and said corresponding longitudinal side.

22. The disposable diaper of claim 21 additionally comprising an elastically contractible gasketing cuff along each of said first and second longitudinal sides, each said elastically contractible gasketing cuff comprising a longitudinal marginal portion and an elastic member operatively associated in an elastically contractible condition with said longitudinal marginal portion, said attachment zone being affixed to the diaper in an area between said proximal edge and said elastic member of said gasketing cuff.

23. The disposable diaper of claim 22 wherein said barrier leg cuff is liquid impermeable.

* * * * *

UNITED STATES PATENT AND TRADEMARK OFFICE
CERTIFICATE OF CORRECTION

PATENT NO. : 5,021,051
DATED : June 4, 1991
INVENTOR(S) : Takashi Hiuke

It is certified that error appears in the above-identified patent and that said Letters Patent is hereby corrected as shown below:

Column 4, line 7, "to o form" should be --to form--.

Column 5, line 40, "marginal o portions" should be --marginal portions--.

Column 9, line 8, "Joined" should be --joined--.

Column 9, line 20, "more o effective" should be --more effective--.

Column 9, line 40, "so a$ to be" should be --so as to be--.

Column 12, line 27, "affixed to the diaper Preferably," should be --affixed to the diaper 10. Preferably,--.

Column 14, line 11, "between said the" should be --between the--.

Column 14, line 48, "(attachment zone)" should be --attachment zone--.

Column 15, line 27, "between said the portion of said barrier cuffs" should be --between the portion of said barrier cuff--.

Signed and Sealed this

Ninth Day of March, 1993

Attest:

STEPHEN G. KUNIN

Attesting Officer

Acting Commissioner of Patents and Trademarks